US011076745B2

(12) United States Patent
Krimsky et al.

(10) Patent No.: US 11,076,745 B2
(45) Date of Patent: Aug. 3, 2021

(54) BRONCHOSCOPY COUPLING DEVICES

(71) Applicant: COVIDIEN LP, Mansfield, MA (US)

(72) Inventors: William S. Krimsky, Forest Hill, MD (US); Joshua B. Stopek, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 890 days.

(21) Appl. No.: 15/606,120

(22) Filed: May 26, 2017

(65) Prior Publication Data

US 2018/0338672 A1    Nov. 29, 2018

(51) Int. Cl.
| | |
|---|---|
| *A61B 1/00* | (2006.01) |
| *A61B 1/018* | (2006.01) |
| *A61B 1/267* | (2006.01) |
| *A61M 39/10* | (2006.01) |
| *A61B 1/01* | (2006.01) |
| *A61B 17/00* | (2006.01) |

(52) U.S. Cl.
CPC ........ *A61B 1/00128* (2013.01); *A61B 1/0014* (2013.01); *A61B 1/00112* (2013.01); *A61B 1/00119* (2013.01); *A61B 1/00121* (2013.01); *A61B 1/00135* (2013.01); *A61B 1/00154* (2013.01); *A61B 1/01* (2013.01); *A61B 1/018* (2013.01); *A61B 1/2676* (2013.01); *A61M 39/105* (2013.01); *A61B 2017/00296* (2013.01)

(58) Field of Classification Search
CPC ............ A61B 1/00128; A61B 1/00154; A61B 1/0014; A61B 1/01; A61B 1/00135; A61B 1/00112; A61B 1/00119; A61B 1/00121; A61B 1/018; A61B 1/2676; A61B 2017/00296; A61M 39/105
See application file for complete search history.

(56) References Cited

U.S. PATENT DOCUMENTS 4,580,556 A  *  4/1986  Kondur ................. A61B 1/267
                                                     128/206.28
5,009,391 A  *  4/1991  Steigerwald ...... A61M 39/0613
                                                        137/849
(Continued)

FOREIGN PATENT DOCUMENTS

| | | |
|---|---|---|
| CN | 103536998 A | 1/2014 |
| CN | 104107027 A | 10/2014 |

(Continued)

OTHER PUBLICATIONS

Partial European Search Report issued in corresponding Appl. No. EP 18174246.1 dated Oct. 23, 2018 (14 pages).

(Continued)

*Primary Examiner* — Timothy J Neal
*Assistant Examiner* — Jae Woo
(74) *Attorney, Agent, or Firm* — Carter, DeLuca & Farrell LLP

(57) ABSTRACT

Provided in accordance with aspects of the present disclosure is a coupling device configured to receive first and second devices. The coupling device may define a first passageway having an inner surface with a first coefficient of friction and defining a first axis. The coupling device may define a second passageway having an inner surface with a second coefficient of friction and defining a second axis, wherein at least a portion of the second axis is at an angle relative to the first axis.

18 Claims, 4 Drawing Sheets

(56) References Cited

U.S. PATENT DOCUMENTS

| | | | | |
|---|---|---|---|---|
| 5,158,569 A * | 10/1992 | Strickland | A61M 16/0463 | 604/533 |
| 5,168,863 A * | 12/1992 | Kurtzer | A61B 1/00142 | 206/363 |
| 5,324,271 A * | 6/1994 | Abiuso | A61M 39/0613 | 604/167.03 |
| 5,359,991 A * | 11/1994 | Takahashi | A61B 1/00142 | 359/510 |
| 5,695,454 A * | 12/1997 | Mourkidou | A61B 1/00142 | 600/121 |
| 5,797,825 A * | 8/1998 | Murata | B23Q 1/4857 | 483/51 |
| 6,458,103 B1 * | 10/2002 | Albert | A61M 39/0613 | 604/165.02 |
| 6,585,639 B1 * | 7/2003 | Kotmel | A61B 1/00082 | 600/114 |
| 6,599,237 B1 * | 7/2003 | Singh | A61B 1/0008 | 600/114 |
| 7,473,219 B1 * | 1/2009 | Glenn | A61B 1/00068 | 600/114 |
| 8,029,473 B2 * | 10/2011 | Carter | A61M 25/0102 | 604/164.05 |
| 8,292,872 B2 * | 10/2012 | Soetermans | A61M 25/09041 | 604/523 |
| 8,317,149 B2 * | 11/2012 | Greenburg | A61B 1/2676 | 248/316.7 |
| 10,004,863 B2 * | 6/2018 | Vazales | A61M 25/10184 | |
| 10,485,406 B2 * | 11/2019 | Lei | A61M 16/0816 | |
| 2001/0021825 A1 * | 9/2001 | Becker | A61M 39/06 | 604/167.01 |
| 2004/0059277 A1 * | 3/2004 | Maguire | A61M 25/10 | 604/6.16 |
| 2005/0059990 A1 * | 3/2005 | Ayala | A61M 25/0662 | 606/192 |
| 2005/0234297 A1 * | 10/2005 | Devierre | A61B 1/00098 | 600/153 |
| 2006/0063973 A1 | 3/2006 | Makower et al. | | |
| 2006/0271152 A1 * | 11/2006 | Hilaire | A61F 2/856 | 623/1.11 |
| 2007/0276180 A1 * | 11/2007 | Greenburg | A61B 1/00128 | 600/106 |
| 2009/0088600 A1 * | 4/2009 | Meloul | A61B 1/00128 | 600/104 |
| 2009/0131751 A1 * | 5/2009 | Spivey | A61B 1/00154 | 600/114 |
| 2009/0306471 A1 * | 12/2009 | Gettman | A61M 25/0662 | 600/104 |
| 2010/0016659 A1 * | 1/2010 | Weitzner | A61B 34/72 | 600/104 |
| 2010/0137681 A1 * | 6/2010 | Ewers | A61B 17/00234 | 600/102 |
| 2011/0022172 A1 * | 1/2011 | Gonzales | A61M 29/02 | 623/10 |
| 2012/0123208 A1 * | 5/2012 | Remmerswaal | A61B 1/267 | 600/116 |
| 2012/0172850 A1 | 7/2012 | Kappel et al. | | |
| 2012/0232339 A1 * | 9/2012 | Csiky | A61B 17/062 | 600/104 |
| 2012/0232553 A1 * | 9/2012 | Bloom | A61B 17/00234 | 606/46 |
| 2012/0241188 A1 * | 9/2012 | Power | A61B 1/00087 | 174/68.3 |
| 2013/0030249 A1 * | 1/2013 | Vazales | A61M 16/04 | 600/120 |
| 2013/0267780 A1 | 10/2013 | Herrmann et al. | | |
| 2014/0005480 A1 | 1/2014 | Wagner et al. | | |
| 2014/0031627 A1 | 1/2014 | Jacobs et al. | | |
| 2015/0073211 A1 | 3/2015 | Dickhans et al. | | |
| 2015/0335228 A1 * | 11/2015 | Lei | A61B 1/00137 | 600/104 |
| 2015/0351613 A1 * | 12/2015 | Knight | A61M 39/1011 | 600/104 |
| 2016/0015255 A1 * | 1/2016 | Dejima | A61B 1/00135 | 600/106 |
| 2016/0051280 A1 * | 2/2016 | Dejima | A61B 1/00087 | 600/114 |
| 2017/0150870 A1 | 6/2017 | Koyama et al. | | |
| 2017/0312000 A1 * | 11/2017 | Auyoung | A61B 17/8855 | |
| 2018/0071481 A1 * | 3/2018 | Snoke | A61B 1/00121 | |
| 2018/0098789 A1 * | 4/2018 | White | A61B 1/055 | |
| 2018/0344142 A1 * | 12/2018 | Abouzgheib | A61B 1/2676 | |
| 2019/0160244 A1 * | 5/2019 | Parry | A61B 1/2676 | |
| 2020/0188035 A1 * | 6/2020 | Amin | A61M 1/008 | |

FOREIGN PATENT DOCUMENTS

| | | |
|---|---|---|
| CN | 106604673 A | 4/2017 |
| WO | 9810822 A1 | 3/1998 |
| WO | 02094087 A1 | 11/2002 |
| WO | 2005025635 A2 | 3/2005 |
| WO | 2016035672 A1 | 3/2016 |

OTHER PUBLICATIONS

Extended European Search Report issued in corresponding Appl. No. EP 18174246.1 dated Mar. 26, 2019 (17 pages).

Office Action issued in corresponding Chinese Appl. No. 201810356742.6 dated Apr. 1, 2020 (9 pages).

* cited by examiner

BRONCHOSCOPY COUPLING DEVICES

BACKGROUND

1. Technical Field

The present disclosure relates to coupling devices for surgical procedures, and more particularly, to coupling devices for managing and securing bronchoscopes, extended working channels, and other surgical instruments during bronchoscopy.

2. Discussion of Related Art

A common interventional procedure in the field of pulmonary medicine is bronchoscopy, in which a bronchoscope is inserted into a patient's airways through the nose or mouth. Bronchoscopes are routinely used in the diagnosis and treatment of lung conditions, such as, lung cancer, airway stenosis, emphysema, etc.

The structure of a bronchoscope generally includes a handle connected to a long, thin, flexible tube that contains a lumen or working channel therethrough for the insertion of instruments therein, such as diagnostic tools (e.g., biopsy tools) or therapeutic tools (e.g., laser, cryogenic, and radio frequency or microwave tissue treatment probes). Rotating a lever on the handle of the bronchoscope actuates a steering mechanism that deflects the distal tip of the bronchoscope in one or more directions such that it may be maneuvered and brought into approximation to target tissue.

During a typical procedure, a clinician holds the bronchoscope handle with one hand and the bronchoscope tube with the other hand, and manipulates the distal tip of the bronchoscope inside the lung by rotating the lever and by pushing and pulling the flexible tube of the bronchoscope. Once the distal tip is directed to target tissue, an instrument may be inserted into the working channel of the bronchoscope to perform a diagnostic or therapeutic procedure. In some situations, an extendable working channel (EWC) is inserted into and through the working channel of the bronchoscope. The EWC defines a smaller diameter permitting access to more remote areas of the lung and a working channel or lumen therethrough for the passage of instruments therein.

One of the challenges of using the working channel of the bronchoscope using either the surgical tools or the EWC is that there is no other channel available for a secondary tool. Further, most attempts at the use of additional tools have resulted in ergonomic and usage challenges for clinicians. Accordingly, there is a need for improvements enabling clinicians to manage, maneuver, retain and/or anchor a bronchoscope and associated surgical tools during bronchoscopy.

SUMMARY

Provided in accordance with aspects of the present disclosure is a coupling device including an elastomeric sheath configured to receive first and second devices. The elastomeric sheath may define a first passageway having an inner surface with a first coefficient of friction and defining a first axis. The elastomeric sheath may define a second passageway having an inner surface with a second coefficient of friction and defining a second axis, wherein at least a portion of the second axis is at an angle relative to the first axis.

In an aspect of the present disclosure, the coupling device is a Y-shaped connector.

In another aspect of the present disclosure, the second axis is angled from the first axis in at least two directions.

In yet another aspect the present disclosure, the second axis is angled from about 30 to about 90 degrees from the first axis in the first direction.

In still another aspect of the present disclosure, the second axis is angled from about 40 to about 70 degrees from the first axis in the first direction.

In still yet another aspect of the present disclosure, the second axis is angled about 45 degrees from the first axis in the first direction.

In another aspect of the present disclosure, the second axis is angled from about 30 to about 90 degrees from the first axis in the second direction.

In yet another aspect of the present disclosure, the second axis is angled from about 40 to about 70 degrees from the first axis in the second direction.

In still another aspect of the present disclosure, the second axis is angled about 45 degrees from the first axis in the second direction.

In still yet another aspect of the present disclosure, wherein the elastomeric sheath is configured such that the first and second devices inserted in the sheath are able to move within the sheath relative to the other.

In another aspect of the present disclosure, the first and second coefficients of friction are the same.

In yet another aspect of the present disclosure, the first coefficient of friction is greater than the second coefficient of friction, such that a first device received in the first passageway is substantially prevented from moving within the sheath while a second device received in the second passageway is slidably retained in the sheath.

In still yet another aspect of the present disclosure, the first passageway is configured to receive a bronchoscope and the second passageway is configured to receive a surgical instrument selected from the group consisting of a saline source, a vacuum source, a catheter, a cannula, an access device, a biopsy tool, and a microwave ablation device.

Provided in accordance with another aspect of the present disclosure is a coupling device including a first portion defining a first annular ring configured to receive a first device, the first annular ring having an inner surface with a first coefficient of friction and defining a first axis, and a second portion defining a second annular ring configured to receive a second device, the second annular ring having an inner surface with a second coefficient of friction and defining a second axis. The second annular ring may extend laterally from the first annular ring such that the first annular ring and the second annular ring are adjoined via a connector.

In another aspect of the present disclosure, the coupling device is dimensioned for passage through airways of a lung.

In yet another aspect of the present disclosure, a sensor may be attached to the coupling device.

In still another aspect of the present disclosure, the second axis is angled from the first axis.

In still yet another aspect of the present disclosure, a locking mechanism is selectively operable to either a locked position or an unlocked position.

Provided in accordance with another aspect of the present disclosure is a surgical tool holder, including a body defining a first passageway configured to operatively connect to an adapter portion of a bronchoscope, the first passageway having an inner surface with a first coefficient of friction and defining a first axis. The body may define a second passageway configured to releasably support a surgical instrument, the second passageway having an inner surface with a second coefficient of friction and defining a second axis that is parallel with the first axis.

In another aspect of the present disclosure, the coupling device is configured to rotate about the adapter portion of the bronchoscope.

BRIEF DESCRIPTION OF THE DRAWINGS

Various aspects and features of the present disclosure are described hereinbelow with references to the drawings, wherein.

DETAILED DESCRIPTION

Figure 1:
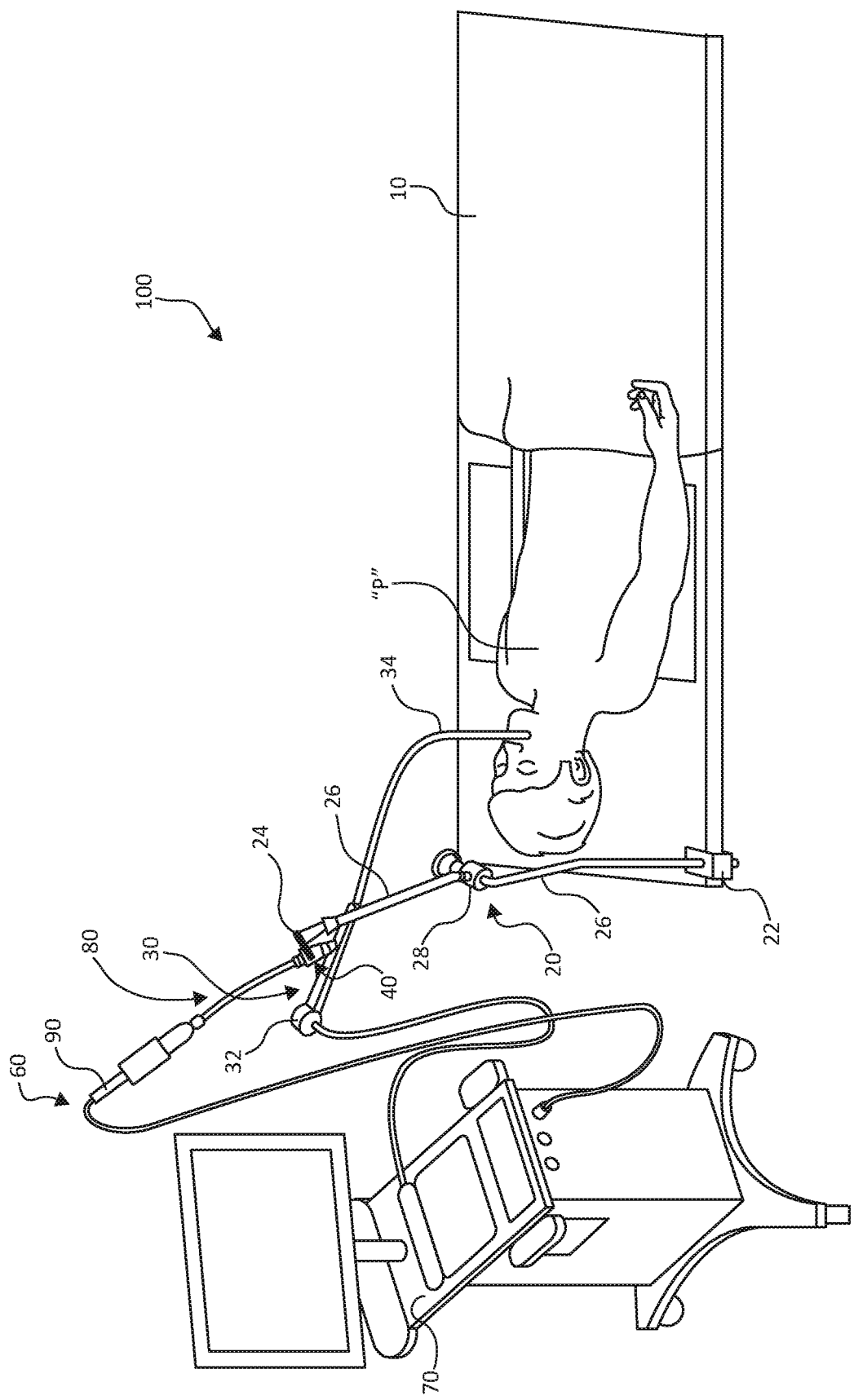
FIG. 1 is a perspective view of a surgical system configured for use with a coupling device in accordance with the present disclosure.

The present disclosure is directed to a coupling device for connecting one or more surgical tools to the outside of a bronchoscope. Once the coupling device is connected to a bronchoscope and the surgical tool, the bronchoscope and the surgical tool can be steered and maneuvered independently of each other. Specifically, the coupling device may be an overtube, ring-like structure, or a tool holder for managing and securing surgical tools to a bronchoscope for improved ergonomics and greater ease of use during bronchoscopic procedures. The coupling device enables the clinician to select from the bronchoscope, an extended working channel or surgical tool passing through the working channel of the bronchoscope, an exterior mounted tool, or combinations of the three for navigation to a desired location within the patient, e.g., airways of the lungs and performing a procedure.

Embodiments of the present disclosure are now described in detail with reference to the drawings in which like reference numerals designate identical or corresponding elements in each of the several views. As is understood in the art, the term "clinician" refers to a doctor, a physician, a nurse, a bronchoscopist, or any other care provider or support personnel. Further, as is understood in the art the term "proximal" refers to the portion of the device or component thereof that is closest to the clinician and the term "distal" refers to the portion of the device or component thereof that is furthest from the clinician.

Referring now to FIG. 1, an exemplary bronchoscopy system 100 is illustrated, which includes a procedure table 10, an external fixture 20, a bronchoscope 30, a bronchoscope adapter 40, one or more surgical tools 60. For the purposes herein, surgical tool 60 will be used to refer to, e.g., a catheter, cannula, access device, biopsy tool, therapeutic tool, saline or vacuum source, EWC 80, microwave ablation device 90, or any other diagnostic or therapeutic surgical tool suitable for bronchoscopy. During a procedure a patient "P" is maintained on procedure table 10 in a supine position, permitting the clinician to insert the distal end (not explicitly shown) of the bronchoscope 30 into a natural opening (e.g., the nose or mouth) or an artificial incision of the patient. Through articulation of a control mechanism 32, and pushing or pulling of a flexible insertion tube 34 of the bronchoscope 30, the distal end of bronchoscope 30 may be directed and steered within the patient towards a target tissue site.

In an exemplary procedure, bronchoscopy system 100 may incorporate a microwave ablation catheter system including a microwave ablation generator 70, the EWC 80, and the microwave ablation device 90. The microwave ablation generator 70 is configured to provide microwave energy to the microwave ablation device 90 for treating/ablating tissue (e.g., tumors) therewith. The EWC 80 is selectively insertable into and through the working channel of bronchoscope 30. The microwave ablation device 90 is configured to be selectively insertable into and through a working channel (not shown) of EWC 80. A proximal portion of EWC 80 extends proximally of bronchoscope adapter 40, where microwave ablation device 90 (or another surgical tool 60) is insertable therein. Utilizing the working channel of the bronchoscope 30, and EWC 80, the microwave ablation device 90 is directed towards target tissue. As should be appreciated, it is desirable to keep the distal end of bronchoscope 30, and/or EWC 80, in proximity to target tissue during insertion and translation of microwave ablation device 90 therethrough.

With continued reference to FIG. 1, external fixture 20 may be coupled to the procedure table 10 for securing, retaining, and/or suspending bronchoscope 30 therewith. Generally, external fixture 20 may include a clamping mechanism 22 for clamping onto table 10, a coupling mechanism 24 for attaching to bronchoscope adapter 40, and one or more suspending arms 26 extending therebetween. A locking articulation joint 28 may couple each suspending arm 26 to one another to permit selective articulation therebetween. It is envisioned that clamping mechanism 22 may be selectively coupled to any number of structures or assemblies within the operating theater, such that external fixture 20 is fixed with respect to the patient "P," such as, for example, to procedure table 10, a surgical table, a robotic arm, a mobile cart, an overhead suspension system, etc. With external fixture 20 secured to an external structure within the operating/procedural theater, bronchoscope 30 may be coupled to coupling mechanism 24. Coupling mechanism 24 may be used to attach to bronchoscope adapter 40 such that bronchoscope 30 is suspended, secured, and/or retained during bronchoscopy. Accordingly, the clinician is not required to hold the bronchoscope 30 for the entirety of the bronchoscopy procedure, and may step away from the bronchoscope 30 as needed to freely move about the operating theater. An example of a coupling mechanism 24 for coupling a bronchoscope to an external fixture is more fully described in U.S. Provisional Patent Application Ser. No. 62/332,097, filed May 20, 2016, and entitled Bronchoscope Coupler, the entire contents of which are hereby incorporated by reference.

As should be appreciated, bronchoscope 30, surgical tools 60, and EWC 80 operate in conjunction to permit navigation to a target site (e.g. airways of the lungs), and presentation of the surgical tools 60 at the target site. The coupling devices described herein permit a clinician to couple additional surgical tools 60 to the outside of bronchoscope 30 for additional functionality when there is no other channel available for a secondary tool, when it is desirable to maintain the working channel free for saline rinsing or application of vacuum suction, a catheter, a cannula, an access device, a biopsy tool, microwave ablation device, or when the desired tool is too large to fit in the working channel of the bronchoscope. In one example, an additional surgical tool 60, such as a biopsy coring tool that may otherwise be too large to fit down the flexible insertion tube 34 of the bronchoscope 30 or the EWC 80, may be coupled to the outside of to the flexible insertion tube 34 of the bronchoscope 30 and inserted into a patient to collect larger biopsy samples than would be possible with tools sized to fit within the bronchoscope working channel. The coupling device may permit the bronchoscope 30 and the additional surgical tool 60 coupled to the bronchoscope 30 to be steered and maneuvered independently of one another. Additionally, the coupling devices in accordance with the present disclosure may be utilized to manage, secure, retain and/or anchor surgical tools 60 to the bronchoscope 30 during bronchoscopy, enabling the surgical tools 60 and/or bronchoscope 30 to be kept free for other uses and from interference with other components of the bronchoscopy system 100, as described herein.

Figure 2:
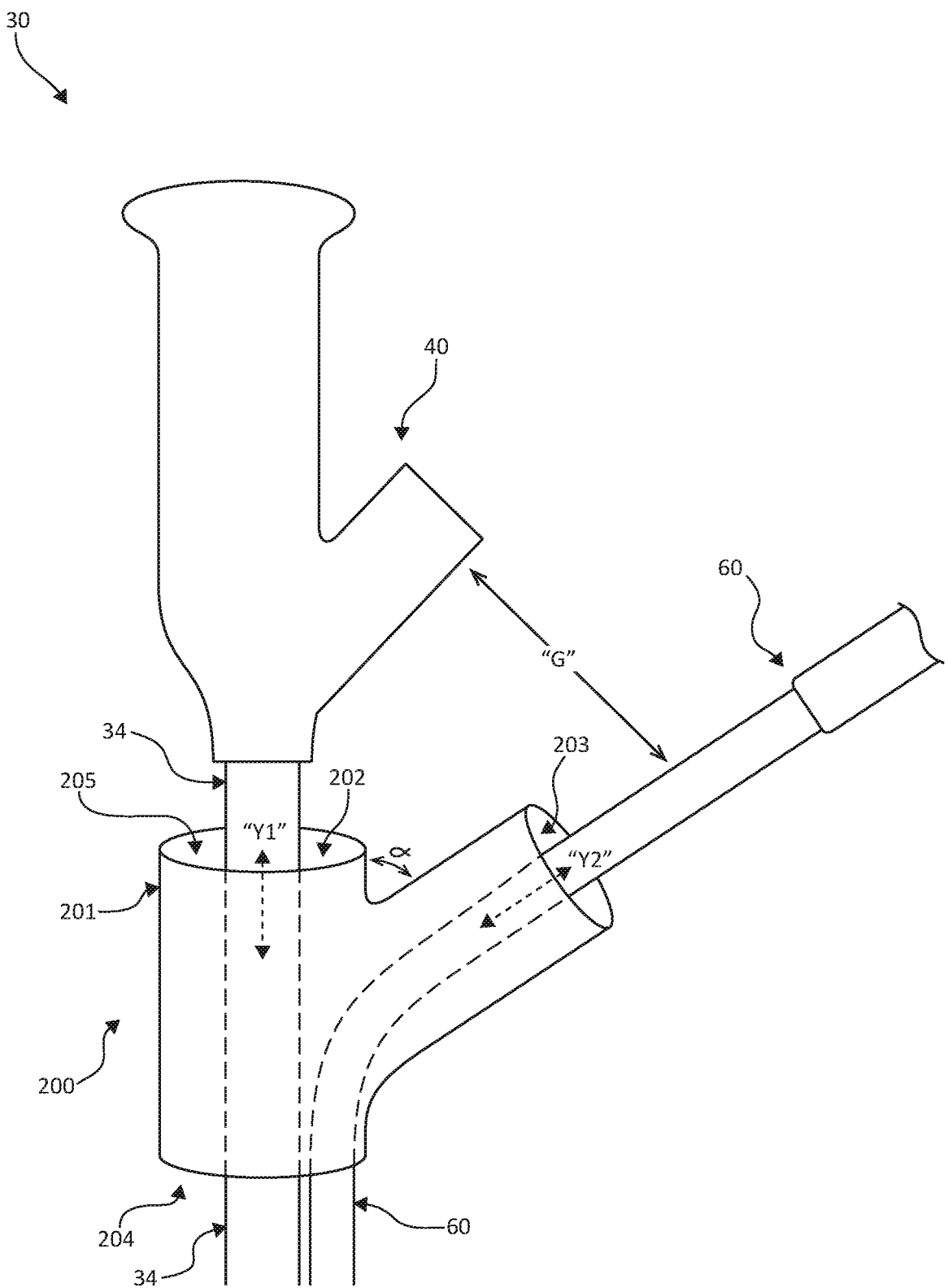
FIG. 2 is a partial perspective view of one illustrative embodiment of a coupling device in the form of an overtube in accordance with the present disclosure.

Referring now to FIG. 2, a coupling device for use with the present disclosure is illustrated and generally identified by reference numeral 200. There is a tendency for bronchoscopes and surgical instruments to tangle or interfere with each other at their respective proximal ends outside of the patient when the clinician moves about the operating theater. Accordingly, coupling device 200 may be a tube or elastomeric sheath configured for receiving, retaining, managing, steering, and securing a surgical tool 60 to a proximal portion of the bronchoscope 30. Coupling device 200 has a body 201 defining a first passageway 202 configured to receive the flexible insertion tube 34 of the bronchoscope 30, and a second passageway 203 configured to receive a surgical tool 60, wherein each of first and second passageways 202, 203, respectively, extend through a distal end 204 of the coupling device 200. Each of the first and second passageways 202, 203 have an inner surface 205. First and second passageways define axes "Y1 and "Y2," respectively.

As can be appreciated, coupling device 200 may be connected to bronchoscope 30 and surgical tool 60 at any time during a procedure. For example, bronchoscope 30 may be inserted into a patient first, upon which the coupling device 200 is then placed over the bronchoscope 30. A surgical tool 60 can then be coupled to the bronchoscope 30 via the coupling device 200. In embodiments, more than one surgical tool 60 may be placed through the first passageway 202 alongside the flexible insertion tube 34 of the bronchoscope 30 or the second passageway 203 of the coupling device 200.

As indicated by a gap "G," coupling device 200 keeps surgical tool 60 and bronchoscope 30 separated such that bronchoscope 30 and surgical tool 60 do not interfere with each other. Additionally, the gap "G" and coupling device 200 enable bronchoscope 30 and surgical tool 60 to be steered and maneuvered independently of each other during a procedure. For example, bronchoscope 30 may be advanced distally into or removed proximally from a patient without interfering with the position of the surgical tool 60. Likewise, surgical tool 60 may be driven or steered independently of bronchoscope 30 without affecting the position of bronchoscope 30. In another embodiment, a surgical tool 60 placed in EWC 80 may be driven within the flexible tube 34 of the bronchoscope 30 without affecting the position of either the bronchoscope 30 or the surgical tool 60 in the first and second passageways 202, 203, respectively. Any combination of the steering, driving, maneuvering of the bronchoscope 30, the surgical tools 60, and/or the EWC 80 is contemplated.

With continued reference to FIG. 2, the axes "Y1" and "Y2" of the first and second passageways 202, 203, respectively, of the coupling device 200 define an angle "α." As can be appreciated, angle "α" may be adjusted to suit a clinician's ergonomic preference. Angle "α" may also affect the maximum gap "G" between the bronchoscope 30 and the surgical instrument 60. In embodiments, axis "Y2" of the second passageway 203 may be angled from axis "Y1" of the first passageway 202 in at least two directions such that axis "Y2" of the second passageway 203 can, e.g., merge, intersect, or align with axis "Y1" of the first passageway 202 at different points. In another embodiment, axis "Y2" of the second passageway 203 is angled in the range from about 20 to about 90 degrees from axis "Y1" of the first passageway 202 in the first direction. In yet another embodiment, the axis "Y2" of the second passageway 203 is angled in the range from about 20 to about 90 degrees from the axis "Y1" of the first passageway 202 in the second direction.

Coupling device 200 may be formed from a flexible material such as an elastomer that permits coupling device 200 to conform to the proximal portions of bronchoscope 30 and the surgical tools 60. As such, coupling device 200 may be an elastomeric sheath that may be, e.g., collapsible. Coupling device 200 may also be rigid, semi-rigid, or the like, and may be formed of any suitable material, such as a thermoplastic or polymer. In embodiments, coupling device 200 may extend only partially over the flexible insertion tube 34 of bronchoscope 30 and the surgical tool 60, as shown in FIG. 2. In other embodiments, the coupling device 200 may extend an additional length, the full length, or greater than the full length of the flexible insertion tube 34 of the bronchoscope 30 and the working channel of the surgical tool 60.

Coupling device 200 is shown as having a Y-shape, but it is contemplated that coupling device 200 may assume any suitable shape. For example, coupling device 200 may have a cylindrical, rectangular, oblong, star, or triangular shape. Additionally or alternatively, coupling device 200 may have additional passageways (e.g., branches) for accommodating additional surgical tools 60.

In embodiments, the inner surface 205 of the coupling device 200 may be formed from or include a frictional surface (e.g., ridged or raised protrusions, high frictional material, etc.) that allows the bronchoscope 30 and/or the surgical tool 60 to remain in place after a clinician has stopped moving the bronchoscope 30 and/or the surgical tool 60. In addition, the clinician is able to step away from the bronchoscopy system 100 without worrying that the bronchoscope 30 and/or surgical tool 60 will become disassociated from each other or that they will change their respective positions (e.g., within the patient or in the operating theater), as last left by the clinician. Additionally or alternatively, the inner surface 205 of the coupling device 200 may be fabricated from a lubricious material to permit the sliding of bronchoscope 30 and surgical tools 60 therein. For example, the inner surface 205 may be fabricated from acetal, nylon, polyphthalamide, polyetheretherketone, and polycarbonate. Alternatively, inner surface 205 may be made lubricious or frictional by virtue of a coating, lining, or the like. In yet another embodiment, inner surface 205 may be formed from or include a combination of frictional and lubricious materials/surfaces. For example, the portion of the inner surface 205 retaining the flexible insertion tube 34 of the bronchoscope 30 may have a frictional fit, while the portion of the inner surface 205 holding the surgical tool 60 may have a lubricious fit.

In embodiments, the inner surface 205 of the first passageway 202 may define a first coefficient of friction and the inner surface 205 of the second passageway 203 may define a second coefficient of friction. The first and second coefficients of friction of the inner surfaces 205 of the first and second passageways 202, 203, respectively, may be the same, or different. For example, the first coefficient of friction of the inner surface 205 of the first passageway 202 may be greater than the second coefficient of friction of the inner surface 205 of the second passageway 203, such that, e.g., bronchoscope 30 received in the first passageway 202 is substantially prevented from moving within the coupling device 200 while the surgical instrument 60 in the second passageway 203 is slidably retained in the coupling device 200. In other embodiments, the coefficient of friction of the inner surface 205 of the second passageway 203 may be greater than the coefficient of friction of the inner surface 205 of the first passageway 202.

Figures 3A, 3B, 3C:
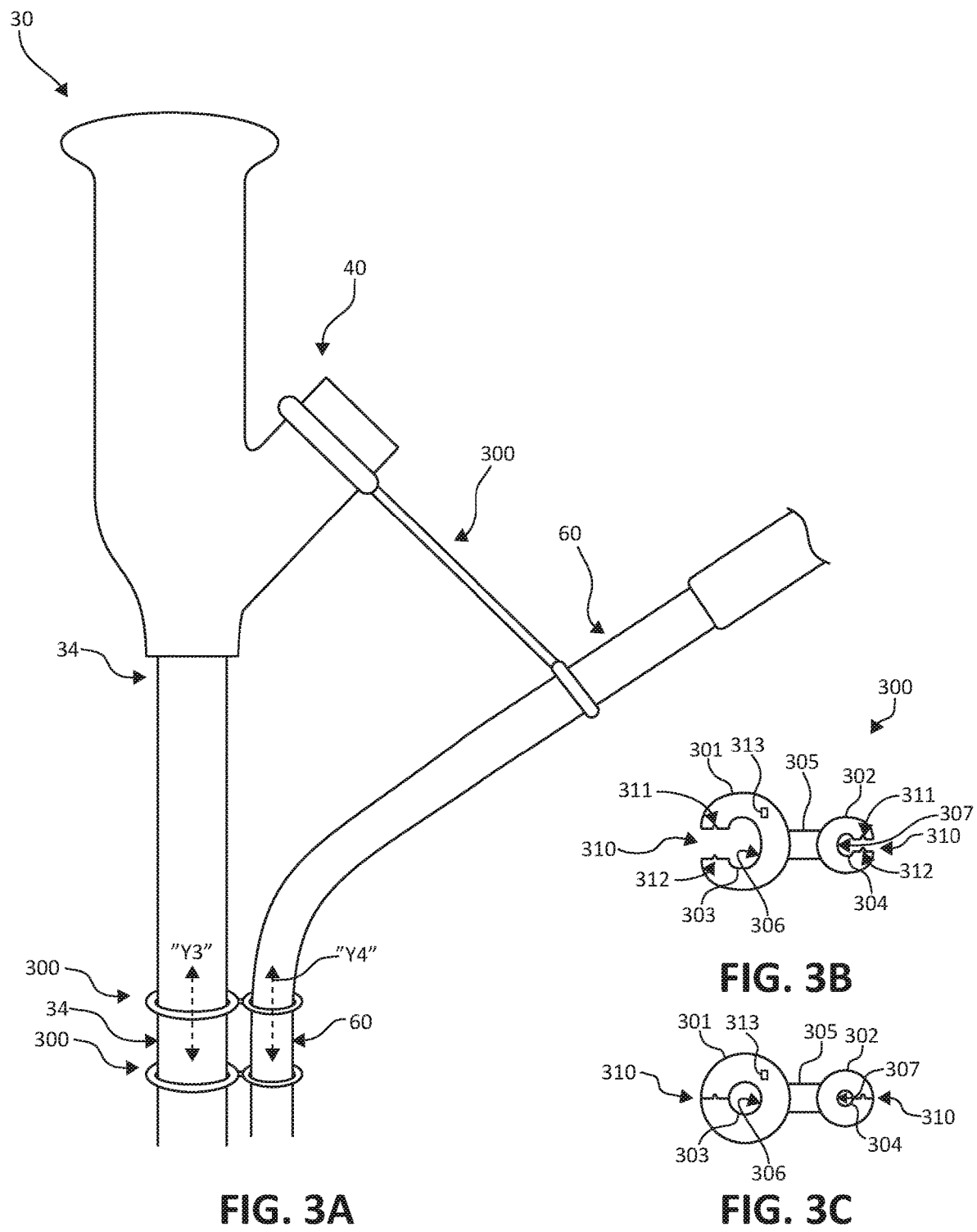
FIG. 3A is a partial, perspective view, of a coupling device in the form of annular rings in accordance with another embodiment of the present disclosure.
FIG. 3B is a top view of the coupling device of FIG. 3A in an unlocked position.
FIG. 3C is a top view of the coupling device of FIG. 3A in a locked position.

Referring now to FIGS. 3A, 3B, and 3C, a coupling device in accordance with another embodiment of the present disclosure is shown and generally designated as 300. One or more coupling devices may be placed anywhere along the flexible insertion tube 34 of the bronchoscope 30, the bronchoscope adapter 40 of the bronchoscope 30, and the working channel of the surgical tool 60. As such, the coupling device 300 may secure the bronchoscope 30 to the surgical tool 60 at any point or points along the bronchoscope 30 and the surgical tool 60. For example, using the coupling device 300 to secure the flexible insertion tube 34 of the bronchoscope 30 to the surgical tool 60 may prevent separation of the flexible insertion tube 34 and the surgical tool 60 within a patient such that they can reach a target site in tandem.

Coupling device 300 may have a first body portion 301 and a second body portion 302 defining a first passageway 303 and a second passageway 304, respectively. First passageway 303 defines a first axis "Y3." Likewise, second passageway 304 defines a second axis "Y4." A connector 305 may be disposed between first and second body portions 301, 302. First axis "Y3" and second axis "Y4" may be parallel to each other, but it is also envisioned that first axis "Y3" may be at an any angle relative to second axis "Y4." The first passageway 303 of first body portion 301 of coupling device 300 may operatively connect to the flexible insertion tube 34 of bronchoscope 30. The second passageway 304 of second body portion 302 of coupling device 300 may operatively connect to surgical tool 60.

With reference to FIGS. 3B and 3C, the coupling device 300 may include a locking mechanism 310 selectively operable to either a locked position or an unlocked position. The locking mechanism 310 is configured to move the first and second body portions 301, 302 such that the coupling device 300 is placed in either a locked position or an unlocked position. The locking mechanism 310 of the coupling device 300 may include at least one recess 311 on a first surface of each of the first and second body portions 301, 302, and at least one protrusion 312 on a second surface of each of the first and second body portions 301, 302. The recesses 311 are engageable with the protrusions 312 to selectively lock or unlock the first and second body portions 301, 302. As such, the combination of the recesses 311 and the teeth 312 of the locking mechanism 310 permits each of the first and second body portions 301, 302 to selectively lock onto the flexible insertion tube 34 of the bronchoscope 30 and/or the working channel of the surgical tool 60 such that the clinician can easily connect or remove the coupling device 300 from the bronchoscope 30 and/or the surgical tool 60.

Connector 305 joins first and second body portions 301, 302. Connector 305 may be made of any suitable size and it is contemplated that the size of connector 305 may be modified such that, e.g., an increase or a decrease in separation between first and second body portions 301, 302 may be achieved. In embodiments, coupling device 300 may be formed from a flexible material such as an elastomer, but it is also contemplated that any rigid or semi-rigid material may be used. First body portion 301, second body portion 302, and connector 305 may be molded such that coupling device 300 is formed as a unitary piece. Alternatively, first body portion 301, second body portion 302, and connector 305 may be formed separately and joined after manufacture.

Coupling device 300 may have an inner surface 306 that defines the first passageway 303 and an inner surface 307 that defines the second passageway 304. Inner surfaces 306, 307 are shown as being annular, but it is contemplated that any suitable shape may be assumed, such as, for example, rectangular, star-shaped, triangular, or the like, and defining first and second passageways 303, 304, respectively. The inner surfaces 306, 307 of the first and second passageways 303, 304 may be fabricated from a frictional or lubricious material, similar to the inner surface 205 described above with respect to coupling device 200, for preventing movement or permitting sliding therein. First and second body portions 301, 302 of coupling device 300 may rotate about their respective axes "Y3," "Y4" for greater maneuvering, steering, and general versatility. In embodiments, inner surface 306 of the first passageway 303 may have a first coefficient of friction and inner surface 307 of the second passageway 304 may have a second coefficient of friction. The first and second coefficients of friction of the inner surfaces 306, 307 of the first and second passageways 303, 304, respectively, may be the same or different, similar to that as described above with respect to coupling device 200.

First and second body portions 301, 302 are shown as being substantially annular or ring-like, but any suitable shape is contemplated. As shown, the second passageway 304 may have a diameter less than that of the first passageway 303. Alternatively (not shown), second passageway 304 may be larger in diameter than first passageway 303, or first and second passageways 303, 304 may be equal in diameter.

In use, one or more coupling devices 300 may be placed anywhere along the flexible insertion tube 34 of bronchoscope 30, the bronchoscope adapter 40 of bronchoscope 30, and/or the surgical tool 60 for coupling therewith. Coupling device 300 may be used in conjunction with, or separately from coupling device 200 for securing, maneuvering, and steering of bronchoscope 30 and surgical tool 60.

In embodiments, coupling device 300 may include a sensor 313 disposed on a surface thereof. Sensor 313 may be placed anywhere on coupling device 300, e.g., on first body portion 301, second body portion 302, or connector 305. The sensor 313 may be, for example, an electromagnetic sensor configured to enhance the navigability of the coupling device 300, the flexible insertion tube 34, or the surgical tool 60 within and through the airways. The sensor 313 may be in communication with the control device (FIG. 1) which provides a real-time indication of the position of the sensor 313 of the coupling device 300 within the airways.

Figure 4B:
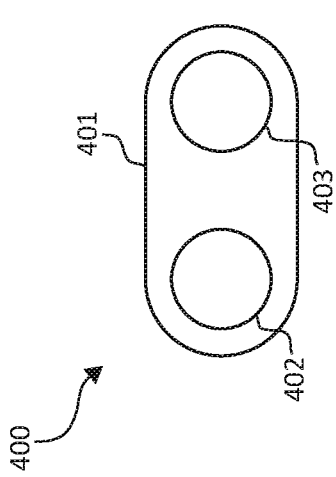
FIG. 4B is a top view of the coupling device of FIG. 4A.
Figure 4C:
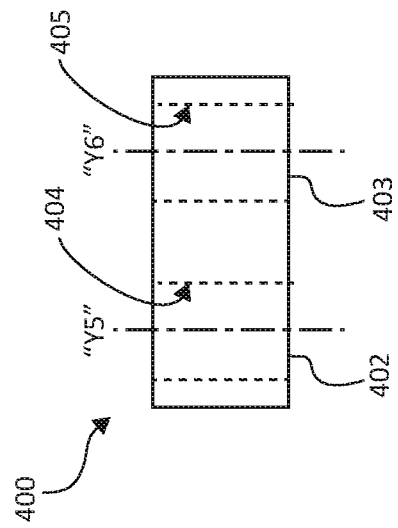
FIG. 4C is a side view of the coupling device of FIGS. 4A and 4B.
Figure 4A:
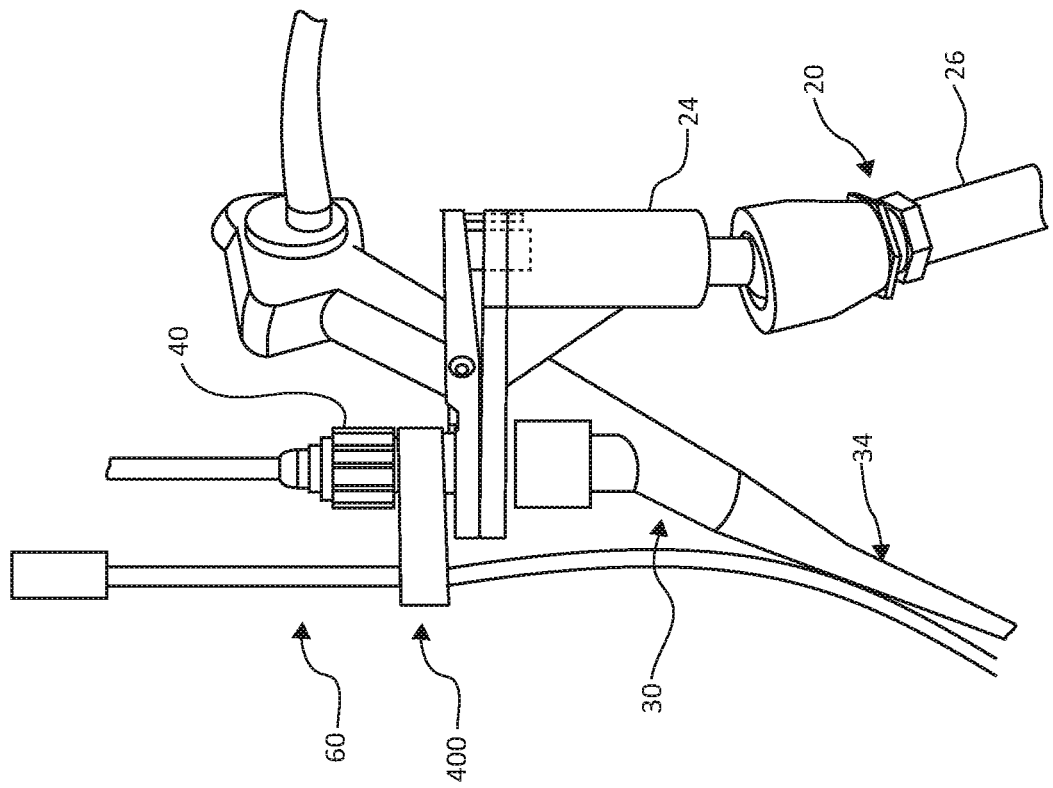
FIG. 4A is a front perspective view of a coupling device in the form of a tool holder in accordance with another embodiment of the present disclosure coupled to a bronchoscope adapter of a bronchoscope.

With reference to FIG. 4A-4C, a coupling device in accordance with another embodiment of the present disclosure is shown and generally designated as 400. Coupling device or tool holder 400 may be used with coupling mechanism 24 (FIGS. 1 and 4A). Tool holder 400 may be used in conjunction with, or separately from, coupling devices 200 and 300 to provide an additional location for placement of surgical tools 60, to minimize tool exchange time, and such that surgical tools 60 do not interfere with or otherwise inhibit a procedure. Tool holder 400 may have a body 401 defining a first passageway 402 therethrough configured to receive the bronchoscope adapter 40. The first passageway 402 may define a first axis "Y5." Body 401 of tool holder 400 may also define a second passageway 403 therethrough configured to receive surgical tools 60. Accordingly, surgical tools 60 can be stored on second passageway 403 of tool holder 400 when not being used or when switching between tools.

The second passageway 403 may define a second axis "Y6" that is parallel with the first axis "Y5" of first passageway 402. It is envisioned that first and second passageways 402, 403 may have any suitable diameters to accommodate bronchoscope adapter 40 and surgical tools 60, respectively. Tool holder 400 may be formed of a substantially rigid or semi-rigid material, but flexible materials are also contemplated. Tool holder 400 may be rotatable about the first axis "Y5" and about bronchoscope adapter 40, such that the position of surgical tools 60 retained in tool holder 400 may be changed relative to bronchoscope 30. As such, a clinician can retain and secure surgical tools 60 or move surgical tools 60 out of the way as necessary.

An inner surface 404 may define the first passageway 402 of tool holder 400 and an inner surface 405 may define the second passageway 403 of tool holder 400. Inner surface 404 of first passageway 402 may be coated with, or fabricated from, a lubricious material to, e.g., facilitate the rotational movement of tool holder 400 about bronchoscope adapter 40. For example, inner surfaces 404, 405 may be fabricated from acetal, nylon, polyphthalamide, polyetheretherketone, polycarbonate, or the like. In other embodiments, inner surface 404 of first passageway 402 may be coated with, or fabricated from a frictional material to prevent movement therein. Inner surfaces 404, 405 may be annular in shape, as depicted. In some embodiments, instead of being annular, inner surfaces 404, 405 may assume any suitable shape, such as, for example, rectangular, triangular, undulating, or the like, defining the corresponding first and second passageways 402, 403, respectively. In embodiments, inner surface 404 of the first passageway 402 may have a first coefficient of friction and inner surface 405 of the second passageway 403 may have a second coefficient of friction. The first and second coefficients of friction of the inner surfaces 404, 405 of the first and second passageways 402, 403, respectively, may be the same or different, similar to that as described above with respect to coupling devices 200 and 300.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A system for coupling a bronchoscope to a surgical tool during a lung procedure, comprising:
   a bronchoscope having an adapter defining a passageway and a flexible insertion tube extending distally from the adapter, the adapter extending from the bronchoscope at an angle relative to a longitudinal axis defined by the bronchoscope, the passageway during use for a lung procedure receiving a catheter and a microwave ablation device therethrough for placement of the microwave ablation device at a target within a patient; and
   a coupling device having an elastomeric sheath defining:
      a first passageway having an inner surface with a first coefficient of friction and defining a first axis, the first passageway including a first proximal opening and a distal opening aligned along the first axis, the first passageway during use for a lung procedure having the flexible insertion tube of the bronchoscope extending therethrough along the first axis and at least one of the catheter or the microwave ablation device extending through the flexible insertion tube along the first axis; and
      a second passageway having an inner surface with a second coefficient of friction and defining a second axis at an angle relative to the first axis, the second passageway including a second proximal opening and sharing the distal opening of the first passageway, the second passageway during use for a lung procedure receiving a surgical tool therethrough such that the surgical tool extends along the second axis into the first passageway and along the first axis, wherein during use for a lung procedure the angle of the second axis relative to the first axis maintains a separation between the bronchoscope and the surgical tool received through the second passageway to enable independent maneuvering of the bronchoscope and the surgical tool relative to each other.

2. The system according to claim 1, wherein the coupling device is a Y-shaped connector.

3. The system according to claim 1, wherein a portion of the second axis is angled from the first axis in at least two directions.

4. The system according to claim 1, wherein the elastomeric sheath is configured such that the flexible insertion tube and the surgical tool inserted in the sheath during use for a lung procedure are able to move within the sheath relative to the other.

5. The system according to claim 1, wherein the first and second coefficients of friction are the same.

6. The system according to claim 1, wherein the first coefficient of friction is greater than the second coefficient of friction, such that during use for a lung procedure the flexible insertion tube received in the first passageway is substantially prevented from moving within the sheath while the surgical tool received in the second passageway is slidably retained in the sheath.

7. The system according to claim 1, wherein the surgical tool is selected from the group consisting of a saline source, a vacuum source, a catheter, a cannula, an access device, a biopsy tool, and a microwave ablation device.

8. A system for coupling a bronchoscope to a surgical tool during a lung procedure, comprising:
   a bronchoscope having an adapter defining a passageway and a flexible insertion tube extending distally from the adapter, the adapter extending from the bronchoscope at an angle relative to a longitudinal axis defined by the bronchoscope, the passageway during use for a lung procedure receiving a catheter and a microwave ablation device therethrough for placement of the microwave ablation device at a target within a patient; and a coupling device having a body defining:

a first passageway configured to operatively connect to the adapter of the bronchoscope, the first passageway having an inner surface with a first coefficient of friction and defining a first axis, the first passageway including a first proximal opening and a distal opening aligned along the first axis, the first passageway during use for a lung procedure having the flexible insertion tube of the bronchoscope extending therethrough along the first axis and at least one of the catheter or the microwave ablation device extending through the flexible insertion tube along the first axis; and a second passageway configured to releasably support a surgical tool, the second passageway having an inner surface with a second coefficient of friction and defining a second axis that is at an angle relative to the first axis, the second passageway including a second proximal opening and sharing the distal opening of the first passageway, the second passageway during use for a lung procedure receiving the surgical tool therethrough such that the surgical tool extends along the second axis into the first passageway and along the first axis, wherein during use for a lung procedure the angle of the second axis relative to the first axis maintains a separation between the bronchoscope and the surgical tool received through the second passageway to enable independent maneuvering of the bronchoscope and the surgical tool relative to each other.

9. The system according to claim 8, wherein the second proximal opening is smaller than the first proximal opening.

10. The system according to claim 8, wherein the second axis is angled from the first axis in at least two directions.

11. The system according to claim 8, wherein the first and second coefficients of friction are the same.

12. The system according to claim 8, wherein the first coefficient of friction is greater than the second coefficient of friction, such that a during use for a lung procedure the flexible insertion tube received in the first passageway is substantially prevented from moving within the body while the surgical tool received in the second passageway is slidably retained in the body.

13. The system according to claim 8, wherein the body is elastomeric.

14. A system for coupling a bronchoscope to a surgical tool during a lung procedure, comprising:

a bronchoscope having an adapter defining a passageway and a flexible insertion tube extending distally from the adapter, the adapter extending from the bronchoscope at an angle relative to a longitudinal axis defined by the bronchoscope, the passageway during use for a lung procedure receiving a catheter and a microwave ablation device therethrough for placement of the microwave ablation device at a target within a patient; and a coupling device having a body defining:

a first passageway defining a first axis and configured to receive a bronchoscope therethrough, the first passageway including:

an inner surface with a first coefficient of friction;
a first proximal opening; and
a distal opening aligned with the first proximal opening along the first axis, the first passageway during use for a lung procedure having the flexible insertion tube of the bronchoscope extending therethrough along the first axis and at least one of the catheter or the microwave ablation device extending through the flexible insertion tube along the first axis; and a second passageway sharing the distal opening of the first passageway, the second passageway configured to receive a surgical tool therethrough and defining a second axis angled from the first axis, the second passageway including:

a second proximal opening smaller than the first proximal opening; and
an inner surface with a second coefficient of friction that is less than the first coefficient of friction;

wherein:

the second passageway during use for a lung procedure receiving the surgical tool therethrough such that the surgical tool extends along the second axis into the first passageway and along the first axis; and during use for a lung procedure the angle of the second axis relative to the first axis maintains a separation between the bronchoscope and the surgical tool received through the second passageway to enable independent maneuvering of the bronchoscope and the surgical tool relative to each other.

15. The system according to claim 14, further comprising an elastomeric body that defines the first and second passageways.

16. The system according to claim 14, wherein the first passageway is configured to connect to the adapter of the bronchoscope.

17. The system according to claim 1, wherein the first passageway is configured to connect to the adapter.

18. The system according to claim 1, wherein the second proximal opening is smaller than the first proximal opening.

* * * * *